ис010562885B2

United States Patent
Inui et al.

(10) Patent No.: US 10,562,885 B2
(45) Date of Patent: Feb. 18, 2020

(54) METHOD FOR PRODUCING TRIAZOLE COMPOUND

(71) Applicant: SUMITOMO CHEMICAL COMPANY, LIMITED, Tokyo (JP)

(72) Inventors: Tomohiko Inui, Osaka (JP); Masaya Tanimoto, Anpachi-gun (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/490,950

(22) PCT Filed: Feb. 21, 2018

(86) PCT No.: PCT/JP2018/006142
§ 371 (c)(1),
(2) Date: Sep. 4, 2019

(87) PCT Pub. No.: WO2018/163818
PCT Pub. Date: Sep. 13, 2018

(65) Prior Publication Data
US 2020/0017468 A1 Jan. 16, 2020

(30) Foreign Application Priority Data
Mar. 6, 2017 (JP) ................ 2017-041353

(51) Int. Cl.
*C07D 401/14* (2006.01)
*C07D 471/04* (2006.01)
(52) U.S. Cl.
CPC ......... *C07D 401/14* (2013.01); *C07D 471/04* (2013.01)
(58) Field of Classification Search
CPC .................. C07D 401/14; C07D 471/04
See application file for complete search history.

(56) References Cited

U.S. PATENT DOCUMENTS

2018/0002345 A1  1/2018  Fischer et al.

FOREIGN PATENT DOCUMENTS

| EP | 3 115 363 A1 | 1/2017 |
| EP | 3 348 554 A1 | 7/2018 |
| WO | WO 2015/133603 A1 | 9/2015 |
| WO | WO 2016/116338 A1 | 7/2016 |
| WO | WO 2016/124563 A1 | 8/2016 |
| WO | WO 2017/043342 A1 | 3/2017 |

OTHER PUBLICATIONS

International Preliminary Report on Patentability and English translation of the Written Opinion of the International Searching Authority dated Sep. 10, 2019 for Application No. PCT/JP2018/ 006142.

International Search Report dated May 1, 2018 for Application No. PCT/JP2018/006142.

*Primary Examiner* — Timothy R Rozof
(74) *Attorney, Agent, or Firm* — Birch, Stewart, Kolasch & Birch, LLP

(57) ABSTRACT

A compound represented by formula (5)

can be produced by simultaneously and separately adding a compound represented by formula (4)

and methanesulfonyl chloride to a compound represented by formula (3)

and a compound represented by formula (6)

(Continued)

having excellent control efficacies against pests can be produced by subjecting the compound represented by formula (5) to intramolecular condensation in the presence of an acid.

4 Claims, No Drawings

METHOD FOR PRODUCING TRIAZOLE COMPOUND

TECHNICAL FIELD

The present invention relates to a method for producing a triazole compound.

BACKGROUND ART

EP3115363A discloses a compound represented by formula (6)

(6)

having pest control efficacies (hereinafter referred to as "Compound (6)").

SUMMARY OF INVENTION

The present invention provides a method for producing the Compound (6).

Also, the present invention provides a method for producing a compound represented by formula (5)

(5)

(hereinafter referred to as "Compound (5)") which is a synthetic intermediate of the Compound (6).

The Compound (5) can be produced by

Step (A): simultaneously and separately adding a compound represented by formula (4)

(4)

(hereinafter referred to as "Compound (4)") and methanesulfonyl chloride to a compound represented by formula (3)

(3)

(hereinafter referred to as "Compound (3)").

The Compound (6) can be produced by

Step (A); and

Step (B): subjecting the Compound (5) to intramolecular condensation in the presence of an acid.

The Compound (3) to be used in the Step (A) can be produced by

Step (C): reacting a compound represented by formula (1)

(1)

[wherein M represents a sodium atom or a potassium atom] (hereinafter referred to as "Compound (1)") with 1H-1,2,4-triazole, namely, a compound represented by formula (2)

(2)

in the presence of an inorganic base, and then mixing the resulting reaction mixture and an acid.

The present invention includes the followings.

[1] A method for producing a compound represented by formula (6), the method comprising Step (A): simultaneously and separately adding the Compound (4) and methanesulfonyl chloride to the Compound (3) to produce the Compound (5); and Step (B): subjecting the Compound (5) to intramolecular condensation in the presence of an acid to produce the Compound (6).

[2] A method for producing the Compound (5), the method comprising

Step (A): simultaneously and separately adding the Compound (4) and methanesulfonyl chloride to the Compound (3) to produce the Compound (5).

[3] The method according to [1] or [2], which comprises Step (C): reacting the Compound (1) with 1H-1,2,4-triazole in the presence of an inorganic base, and then mixing the resulting reaction mixture and an acid to produce the Compound (3).

DESCRIPTION OF EMBODIMENTS

In the present description and the others, Me represents a methyl group and Et represents an ethyl group.

First, the Step (A) is described.

In the Step (A), the Compound (4) and methanesulfonyl chloride are simultaneously and separately added to the Compound (3) to produce the Compound (5).

Here, the simultaneous and separate addition of the Compound (4) and methanesulfonyl chloride to the Compound (3) is carried out in control of the conditions such as addition rate (for example, drop rate) so that the molar ratio of the Compound (4) and methanesulfonyl chloride can be maintained close to 1:1, specifically within the range of 1:0.5 to 1:2, preferably 1:0.8 to 1:1.3 in the reaction system of the Step (A) (namely, a composition obtained by adding dropwise the Compound (4) and methanesulfonyl chloride to the Compound (3)).

The simultaneous and separate addition of the Compound (4) and methanesulfonyl chloride to the Compound (3) may be carried out by, for example, adding the Compound (4) and methanesulfonyl chloride from separate addition ports to the Compound (3) in a container.

The Compound (3) is usually mixed with a solvent and used as a liquid composition.

Examples of the solvent include inert solvents such as ethers such as 1,4-dioxane, diethyl ether, tetrahydrofuran (THF), tert-butyl methyl ether, cyclohexyl methyl ether, ethylene glycol dimethyl ether, and diethylene glycol dimethyl ether; halogenated hydrocarbons such as dichloromethane, chloroform, carbon tetrachloride, 1,2-dichloroethane, and chlorobenzene; aromatic hydrocarbons such as toluene, benzene, xylene, and ethylbenzene; nitriles such as acetonitrile; aprotic polar solvents such as N,N-dimethylformamide (DMF), N,N-dimethylacetamide, N-methyl-2-pyrrolidone (NMP), 1,3-dimethyl-2-imidazolidinone, sulfolane, and dimethylsulfoxide (DMSO); nitrogen-containing aromatic compounds such as pyridine and quinoline; and mixtures thereof.

In the addition of the Compound (4), it is usually mixed with a solvent and used as a solution. Examples of the solvent are the same as those to be mixed with the Compound (3) described above.

Methanesulfonyl chloride may also be used after diluting it with a solvent. Examples of the solvent include inert solvents such as ethers such as 1,4-dioxane, diethyl ether, THF, tert-butyl methyl ether, cyclohexyl methyl ether, ethylene glycol dimethyl ether, and diethylene glycol dimethyl ether; halogenated hydrocarbons such as dichloromethane, chloroform, carbon tetrachloride, 1,2-dichloroethane, and chlorobenzene; aromatic hydrocarbons such as toluene, benzene, xylene, and ethylbenzene; nitriles such as acetonitrile; and mixtures thereof.

The reaction of the Step (A) is preferably carried out in the presence of a base.

The base is usually added to the solution of the Compound (4) in advance.

Examples of the base include tertiary amines such as triethylamine and N,N-diisopropylethylamine; and nitrogen-containing aromatic compounds such as pyridine and 4-dimethylaminopyridine.

In the reaction, the Compound (4) is usually used at a ratio of 0.5 to 2 mol, preferably 0.8 to 1.5 mol, relative to 1 mol of the Compound (3).

In the reaction, methanesulfonyl chloride is usually used at a ratio of 0.5 to 2 mol, preferably 0.8 to 1.5 mol, relative to 1 mol of the Compound (3).

When a base is used in the reaction, the base is usually used at a ratio of 0.5 to 5 mol, preferably 0.8 to 3 mol, relative to 1 mol of the Compound (3).

The reaction temperature is usually within the range of −10 to 80° C., preferably 0 to 60° C.

The reaction time is usually within the range of 0.1 to 24 hours, preferably 1 to 20 hours.

After the reaction is completed, the reaction mixture may be subjected to a work-up such as mixing the reaction mixture and water, then carrying out extraction with an organic solvent, and drying or concentrating the resulting organic layer; mixing the reaction mixture and water, and collecting the resulting solids by filtration; mixing the reaction mixture, an aqueous solution of an alkali metal hydroxide (for example, sodium hydroxide or potassium hydroxide), and water, and collecting the resulting solids by filtration; and collecting the solids produced in the reaction mixture by filtration, to isolate the Compound (5). The isolated Compound (5) may be further purified by chromatography, recrystallization, or the like.

The reaction mixture comprising the Compound (5) may also be directly subjected to the next reaction to produce the Compound (6).

Next, the Step (B) is described.

In the Step (B), the Compound (5) produced in the Step (A) is subjected to intramolecular condensation in the presence of an acid to produce the Compound (6).

The reaction of the Step (B) is usually carried out in a solvent.

Examples of the solvent include alcohols such as 2-butanol, ethylene glycol, propylene glycol, dipropylene glycol (a mixture of 4-oxa-2,6-heptanediol, 2-(2-hydroxypropoxy)propan-1-ol, and 2-(2-hydroxy-1-methylethoxy)propan-1-ol), 1,3-butanediol, glycerin, and polyethylene glycols having average molecular weight of 200 to 400; ketones such as methyl isobutyl ketone; ethers such as 1,4-dioxane and diethylene glycol dimethyl ether; halogenated hydrocarbons such as chlorobenzene; aromatic hydrocarbons such as toluene, benzene, xylene, and ethylbenzene; nitriles such as propionitrile; aprotic polar solvents such as DMF, NMP, N,N-dimethylacetamide, 1,3-dimethyl-2-imidazolidinone, and DMSO; water; and mixtures thereof.

Examples of the acid include sulfonic acids such as p-toluenesulfonic acid; carboxylic acids such as acetic acid and lactic acid; and inorganic acids such as sulfuric acid, phosphoric acid, and polyphosphoric acid. Also, methanesulfonic acid, which is produced in the reaction system in a work-up of the reaction mixture obtained in the Step (A) by mixing the reaction mixture and water, and reacting methanesulfonyl chloride with water, may be used.

In the reaction, the acid is usually used at a ratio of 0.1 to 5 mol relative to 1 mol of the Compound (5).

The amount of the acid to be used is usually at a ratio of 1 to 5 part(s) by weight relative to 1 part by weight of the Compound (5). When a liquid acid such as acetic acid and lactic acid is used, the acid itself may also be used as a solvent.

The reaction temperature is usually within the range of 100 to 200° C.

The reaction time is usually within the range of 0.1 to 48 hours.

After the reaction is completed, the reaction mixture may be subjected to a work-up such as mixing the reaction mixture and water, then carrying out extraction with an organic solvent, and concentrating the resulting organic layer; mixing the reaction mixture and water, and collecting the resulting solids by filtration; and collecting the solids produced in the reaction mixture by filtration, to isolate the Compound (6). The isolated Compound (6) may also be further purified by recrystallization, chromatography, or the like.

Next, the Step (C) is described.

In the Step (C), the Compound (1) is reacted with 1H-1,2,4-triazole in the presence of an inorganic base, and then mixing the resulting reaction mixture and an acid to produce the Compound (3).

The reaction of the Step (C) is usually carried out in a solvent.

Examples of the solvent include water; ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; aromatic hydrocarbons such as toluene, benzene, xylene, and ethylbenzene; esters such as ethyl acetate and butyl acetate; nitriles such as acetonitrile; aprotic polar solvents such as DMF, N,N-dimethylacetamide, NMP, 1,3-dimethyl-2-imidazolidinone, and DMSO; nitrogen-containing aromatic compounds such as pyridine and quinoline; and mixtures thereof.

Examples of the inorganic base include alkali metal hydrides such as sodium hydride and potassium hydride; alkali metal carbonates such as sodium carbonate and potassium carbonate; and alkali metal hydroxides such as potassium hydroxide and sodium hydroxide.

In the reaction, 1H-1,2,4-triazole is usually used at a ratio of 1 to 2 mol, and the inorganic base is usually used at a ratio of 1 to 5 mol, relative to 1 mol of the Compound (1).

The reaction temperature is usually within the range of 0 to 120° C.

The reaction time is usually within the range of 0.1 to 24 hours.

The Compound (1) is reacted with 1H-1,2,4-triazole, and then the resulting reaction mixture is mixed with an acid. The amount of the acid to be used is usually at a ratio of 2 to 8 mol relative to 1 mol of the Compound (1).

When solids are produced by mixing the reaction mixture with the acid, the resulting solids may be collected by filtration to isolate the Compound (3). When a solid is not produced by mixing the reaction mixture with the acid, the reaction mixture may be subjected to a work-up such as carrying out extraction with an organic solvent, then concentrating the resulting organic layer to isolate the Compound (3). The isolated Compound (3) may also be further purified by recrystallization, chromatography, or the like.

Examples of the acid to be used include hydrochloric acid and sulfuric acid.

EXAMPLES

The following Examples serve to illustrate the present invention more in detail, which should not intend to limit the present invention. In the following Examples and the like, "%" means "% by weight" unless otherwise specified.

In the following Examples, quantitative analyses were carried out by using high performance liquid chromatography unless otherwise specified. The analysis conditions are as follows.

[High Performance Liquid Chromatography Analysis Conditions 1]
  Internal standard material: isopropyl benzoate
  Mobile phase: Solution A: 0.1% phosphoric acid aqueous solution, Solution B: acetonitrile
  Solution A/Solution B=65/35 (v/v)
  Column: SUMIPAX (registered trademark) ODS Z-CLUE, Particle size 3 μm, 4.6 mm I.D.×100 mm
  UV measurement wavelength: 254 nm
  Flow rate: 1.0 mL/min
  Column oven: 40° C.
  Injection volume: 10 μL

[High Performance Liquid Chromatography Analysis Conditions 2]
  Internal standard material: biphenyl
  Mobile phase: Solution A: 0.1% phosphoric acid aqueous solution, Solution B: acetonitrile
  Gradient conditions: see the following Table 1
  Column: SUMIPAX (registered trademark) ODS Z-CLUE, Particle size 3 μm, 3.0 mm I.D.×100 mm
  UV measurement wavelength: 254 nm
  Flow rate: 1.0 mL/min
  Column oven: 40° C.
  Injection volume: 10 μL
<Gradient Conditions>

TABLE 1

| Time (min) | Solution B in mobile phase (%) |
|---|---|
| 0.00 | 10 |
| 30.00 | 90 |
| 35.00 | 90 |
| 35.01 | 10 |
| 40.00 | Stop |

[High Performance Liquid Chromatography Analysis Conditions 3]
  Mobile phase: Solution A: 0.05% trifluoroacetic acid aqueous solution, Solution B: acetonitrile
  Gradient conditions: see the following Table 2
  Column: SUMIPAX (registered trademark) ODS Z-CLUE, Particle size 3 μm, 4.6 mm I.D.×100 mm
  UV measurement wavelength: 260 nm
  Flow rate: 1.0 mL/min
  Column oven: 40° C.
  Injection volume: 10 μL
<Gradient Conditions>

TABLE 2

| Time (min) | Solution B in mobile phase (%) |
|---|---|
| 0 | 5 |
| 5 | 5 |
| 45 | 80 |
| 45.01 | 5 |
| 60 | Stop |

Example 1

Under nitrogen atmosphere, the Compound (4) (29.4 g, 154 mmol), NMP (43.4 g), and triethylamine (34.2 g) were mixed at room temperature. Each of the resulting mixture and methanesulfonyl chloride (22.0 g, 192 mmol) was simultaneously and separately added dropwise to a mixture of the Compound (3) (45.6 g, 161 mmol) and NMP (86.8 g) at 12° C. over 5 hours, and each addition was simultaneously completed. Each drop rate of the Compound (4) and methanesulfonyl chloride was controlled so that any one of them would not be inappropriately excessively added, each addition of the Compound (4) and methanesulfonyl chloride would be simultaneously started, roughly constant drop rate would be maintained, and each addition would be simultaneously completed. Subsequently, the resulting mixture was stirred at 12° C. for 17 hours. The resulting mixture was analyzed by high performance liquid chromatography using isopropyl benzoate as an internal standard material (High performance liquid chromatography analysis conditions 1) to confirm that the yield of the Compound (5) was 98.4%.

Each of the resulting mixture and a 48% potassium hydroxide aqueous solution (9.2 g) was simultaneously and separately added dropwise to water (251.1 g) maintained at 50° C. over 3 hours. During the addition, the drop rate was controlled so that the pH of the slurry in the flask would be maintained between 4 and 8. The resulting slurry was cooled to 25° C. over 2 hours, and then the resulting solids were filtered. The filtered solids were washed twice with water (132.3 g), and then dried under reduced pressure to give the Compound (5) as white solids (72.7 g, content 91.4%, yield 94.9%). The yield was measured by the High performance liquid chromatography analysis conditions 1 using isopropyl benzoate as an internal standard material.

Compound (5): $^1$H-NMR (DMSO-$D_6$) δ: 10.46 (1H, br s), 9.84 (1H, s), 8.68 (1H, d, J=8.6 Hz), 8.48 (1H, s), 8.38-8.37 (1H, br m), 8.25 (1H, d, J=8.6 Hz), 7.93 (1H, d, J=2.3 Hz), 6.66-6.64 (1H, br m), 3.72 (2H, q, J=7.4 Hz), 2.95 (3H, d, J=4.8 Hz), 1.22 (3H, t, J=7.4 Hz)

Example 2

Under nitrogen atmosphere, the Compound (5) (0.20 g), concentrated sulfuric acid (45 mg), water (0.20 g), and DMF (0.40 g) were mixed at room temperature, the resulting mixture was warmed to 120° C., and stirred for 9 hours. To the resulting mixture was added water, the resulting solids were filtered, washed with water, and then dried under reduced pressure. The solids were analyzed by high performance liquid chromatography using biphenyl as an internal standard material (High performance liquid chromatography analysis conditions 2) to confirm that the Compound (6) was obtained as white solids (yield 86.4%). Compound (6): $^1$H-NMR (CDCl$_3$) δ: 9.16 (1H, s), 8.81 (1H, br s), 8.72 (1H, d), 8.36 (1H, br s), 8.31 (1H, d), 8.21 (1H, s), 3.93 (3H, s), 3.82 (2H, q), 1.39 (3H, t)

Example 3

Under nitrogen atmosphere, the Compound (5) (1.83 g), a 90% lactic acid aqueous solution (1.00 g), and propylene glycol (4.00 g) were mixed at room temperature, the resulting mixture was warmed to 120° C., and stirred for 12 hours. The resulting mixture was cooled to 85° C., water (5.00 g) was added thereto, and then the resulting mixture was stirred at 85° C. for 30 minutes. The resulting mixture was cooled to room temperature, the resulting solids were filtered, washed with water (5.00 g), and then dried under reduced pressure to give the Compound (6) (1.78 g, content 92.6%, yield 93.8%: measured by the High performance liquid chromatography analysis conditions 2 using biphenyl as an internal standard material).

Example 4

Under nitrogen atmosphere, a mixture of the Compound (5) and water (water content 61.6%) (76.12 g), a 90% lactic acid aqueous solution (15.58 g), and propylene glycol (85.58 g) were mixed at room temperature. The resulting mixture was heated in a bath at 135° C. to be dehydrated until the internal temperature became 120° C., and stirred for 11 hours. The resulting mixture was cooled to 75° C., water (142.46 g) was added thereto, and then the resulting mixture was stirred at 75° C. for 30 minutes. The resulting mixture was cooled to 40° C., the resulting solids were filtered, washed twice with water (143 g), and then dried under reduced pressure to give the Compound (6) (24.54 g, content 98.53%, yield 86.9%: measured by the High performance liquid chromatography analysis conditions 1 using isopropyl benzoate as an internal standard material).

Example 5

Under nitrogen atmosphere, the Compound (5) (1.83 g) and a 90% lactic acid aqueous solution (4.00 g) were mixed at room temperature, the resulting mixture was warmed to 120° C., and stirred for 10 hours. The resulting mixture was cooled to 85° C., water (5.00 g) was added thereto, and then the resulting mixture was stirred at 85° C. for 30 minutes. The resulting mixture was cooled to room temperature, the resulting solids were filtered, washed with water (5.00 g), and then dried under reduced pressure to give the Compound (6) (1.80 g, content 87.8%, yield 89.5%: measured by the High performance liquid chromatography analysis conditions 2 using biphenyl as an internal standard material).

Example 6

Under nitrogen atmosphere, the Compound (5) (1.83 g), a 90% lactic acid aqueous solution (1.00 g), and xylene (4.00 g) were mixed at room temperature, the resulting mixture was warmed to 150° C., and stirred for 10 hours. The resulting mixture was concentrated, to the resulting residue was added water (5.00 g) at room temperature, and the resulting mixture was stirred for 30 minutes. The resulting solids were filtered, washed with water (5.00 g), and then dried under reduced pressure to give the Compound (6) (1.68 g, content 89.3%, yield 85.2%: measured by the High performance liquid chromatography analysis conditions 2 using biphenyl as an internal standard material).

Example 7

Under nitrogen atmosphere, the Compound (5) (1.83 g), a 90% lactic acid aqueous solution (1.00 g), and methyl isobutyl ketone (4.00 g) were mixed at room temperature, the resulting mixture was warmed to 120° C., and stirred for 43 hours. The resulting mixture was concentrated, to the resulting residue was added water (5.00 g) at room temperature, and the resulting mixture was stirred for 30 minutes. The resulting solids were filtered, washed with water (5.00 g), and then dried under reduced pressure to give the Compound (6) (1.65 g, content 84.6%, yield 79.5%: measured by the High performance liquid chromatography analysis conditions 2 using biphenyl as an internal standard material).

Example 8

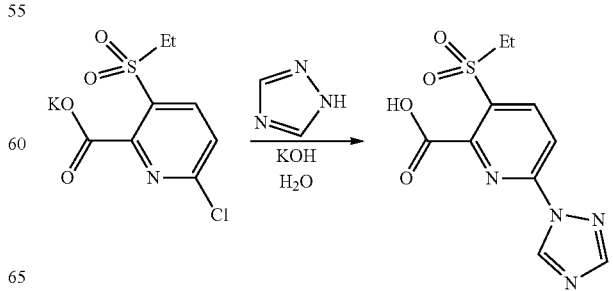

Under nitrogen atmosphere, a potassium 6-chloro-3-(ethanesulfonyl)-2-pyridinecarboxylate aqueous solution (content: 38.9%) (200.00 g), 1H-1,2,4-triazole (37.70 g), and potassium hydroxide (21.26 g) were mixed at room temperature, the resulting mixture was warmed to 85° C., and stirred for 9 hours. The resulting mixture was cooled to 55° C., then water (194.35 g) was added thereto, and then concentrated sulfuric acid (59.48 g) was added dropwise thereto at 55° C. over 6 hours. The resulting mixture was cooled to 20° C., the resulting solids were filtered, washed with water (116.6 g), and then dried under reduced pressure to give the Compound (3) as white solids (yield 96.1%). The yield was measured by absolute calibration curve method using the High performance liquid chromatography analysis conditions 3.

Compound (3): $^1$H-NMR (CDCl$_3$) δ: 9.42 (1H, s), 8.56 (1H, d, J=8.6 Hz), 8.23 (1H, s), 8.18 (1H, d, J=8.6 Hz), 3.62 (2H, q, J=7.5 Hz), 1.36 (3H, t, J=7.5 Hz).

Example 9

Under nitrogen atmosphere, a potassium 6-chloro-3-(ethanesulfonyl)-2-pyridinecarboxylate aqueous solution (content: 38.9%) (150.10 g) and 1H-1,2,4-triazole (28.27 g) were mixed at room temperature, and the resulting mixture was warmed to 85° C. To the resulting mixture was added dropwise a 48% potassium hydroxide aqueous solution (33.26 g) at 85° C. over 3.5 hours, and then the resulting mixture was stirred at 85° C. for 5 hours. The resulting mixture was cooled to 55° C., and then added dropwise to a mixture of water (145.8 g) and concentrated sulfuric acid (44.61 g) maintained at 55° C. over 4 hours. The resulting mixture was cooled to 20° C., the resulting solids were filtered, washed with water (87.5 g), and then dried under reduced pressure to give the Compound (3) as white solids (yield 96.9%). The yield was measured by absolute calibration curve method using the High performance liquid chromatography analysis conditions 3.

Reference Example 1

Under nitrogen atmosphere, the Compound (3) (46.3 g), the Compound (4) (29.9 g), NMP (138.9 g), and triethylamine (34.8 g) were mixed at room temperature. To the resulting mixture was added dropwise methanesulfonyl chloride (22.4 g) at 10° C. over 5 hours, and then the resulting mixture was stirred at 10° C. for 17 hours. The resulting mixture was analyzed by high performance liquid chromatography using isopropyl benzoate as an internal standard material (High performance liquid chromatography analysis conditions 1) to confirm that the yield of the Compound (5) was 62.3%.

The resulting mixture was added dropwise to water (268.3 g) maintained at 50° C. over 5 hours. The resulting slurry was cooled to 25° C. over 2 hours, and then the resulting solids were filtered. The filtered solids were washed twice with water (134.4 g), and then dried under reduced pressure to give the Compound (5) as white solids (yield 59.9%). The yield was measured by the High performance liquid chromatography analysis conditions 1 using isopropyl benzoate as an internal standard material.

INDUSTRIAL APPLICABILITY

According to the method of the present invention, the Compound (6) having pest control efficacies and a synthetic intermediate thereof, the Compound (5), can be produced.

The invention claimed is:

1. A method for producing a compound represented by formula (6)

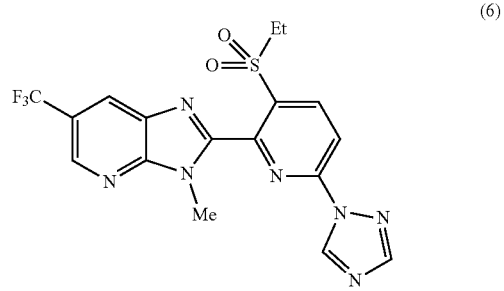 [SMILES: CCS(=O)(=O)c1ccc(-n2cncn2)nc1-c1nc2cc(C(F)(F)F)cnc2n1C]

the method comprising

Step (A): simultaneously and separately adding a compound represented by formula (4)

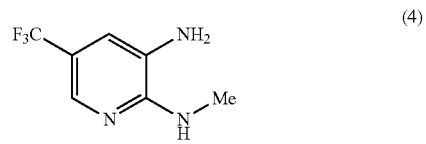

and methanesulfonyl chloride to a compound represented by formula (3)

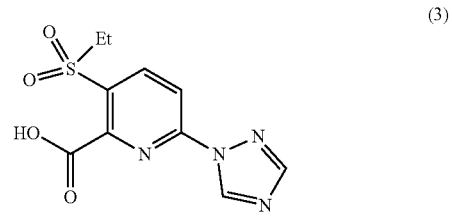 [SMILES: CCS(=O)(=O)c1ccc(-n2cncn2)nc1C(=O)O]

to produce a compound represented by formula (5)

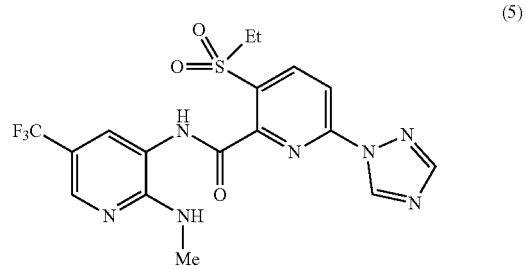 [SMILES: CCS(=O)(=O)c1ccc(-n2cncn2)nc1C(=O)Nc1cc(C(F)(F)F)cnc1NC]

and

Step (B): subjecting said compound represented by formula (5) to intramolecular condensation in the presence of an acid to produce the compound represented by formula (6).

2. The method according to claim 1, which comprises Step (C): reacting a compound represented by formula (1)

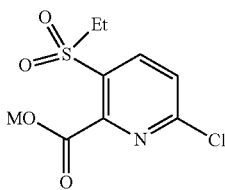
(1)

[wherein M represents a sodium atom or a potassium atom] with 1H-1,2,4-triazole in the presence of an inorganic base, and then mixing the resulting reaction mixture and an acid to produce the compound represented by formula (3);
Step (A); and
Step (B).

3. A method for producing a compound represented by formula (5)

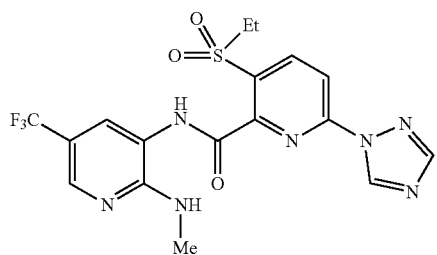
(5)

the method comprising
Step (A): simultaneously and separately adding a compound represented by formula (4)

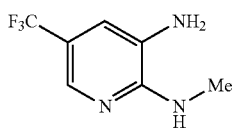
(4)

and methanesulfonyl chloride to a compound represented by formula (3)

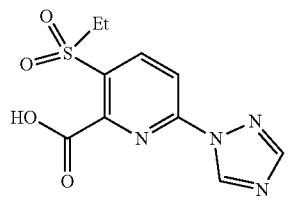
(3)

to produce a compound represented by formula (5).

4. The method according to claim 3, which comprises Step (C): reacting a compound represented by formula (1)

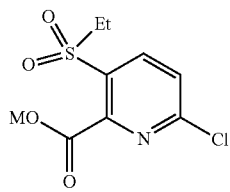
(1)

[wherein M represents a sodium atom or a potassium atom] with 1H-1,2,4-triazole in the presence of an inorganic base, and then mixing the resulting reaction mixture and an acid to produce the compound represented by formula (3); and
Step (A).

* * * * *